(12) United States Patent
Murata et al.

(10) Patent No.: US 8,303,820 B2
(45) Date of Patent: Nov. 6, 2012

(54) METHOD OF PURIFYING CYTIDINE DIPHOSPHATE CHOLINE

(75) Inventors: Hideki Murata, Hofu (JP); Tsuyoshi Mokudai, Hofu (JP); Michio Shiomi, Yamabu-gun (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 1146 days.

(21) Appl. No.: 12/063,318

(22) PCT Filed: Aug. 10, 2006

(86) PCT No.: PCT/JP2006/315802
§ 371 (c)(1),
(2), (4) Date: Feb. 8, 2008

(87) PCT Pub. No.: WO2007/018259
PCT Pub. Date: Feb. 15, 2007

(65) Prior Publication Data
US 2009/0286284 A1    Nov. 19, 2009

(30) Foreign Application Priority Data
Aug. 10, 2005  (JP) ................. 2005-231958

(51) Int. Cl.
*B01D 19/30* (2006.01)
*B01D 15/36* (2006.01)
*B01J 39/12* (2006.01)
*C12P 19/30* (2006.01)
*C07H 19/10* (2006.01)

(52) U.S. Cl. .......... 210/660; 435/89; 536/26.8

(58) Field of Classification Search ........ 210/660; 435/89; 536/26.8
See application file for complete search history.

(56) References Cited

U.S. PATENT DOCUMENTS

| | | | |
|---|---|---|---|
| 4,560,661 A | 12/1985 | Katsumata et al. | |
| 5,589,517 A | 12/1996 | Sugawara et al. | |
| 6,387,667 B1 | 5/2002 | Maruyama et al. | |
| 7,226,767 B2 | 6/2007 | Maruyama et al. | |
| 2004/0267005 A1* | 12/2004 | Yerxa et al. ............... | 536/26.1 |

FOREIGN PATENT DOCUMENTS

| | | |
|---|---|---|
| EP | 1 502 956 A1 | 2/2005 |
| GB | 1 305 539 | 2/1973 |
| JP | 63-6558 B2 | 2/1988 |
| JP | 6-31306 B2 | 4/1994 |
| WO | WO 99/49073 A1 | 9/1999 |

OTHER PUBLICATIONS

English translation of JP 62-016497, Takeda Pharm. Co., Ltd., Method for purifying cytidine-5'-diphosphoric acid choline, 1987.*
Diaion® cation exchange resins, Diaion CationTable E, http://www.diaion.com/Diaion_Tables/Diaion_CationTable_R_E.htm, 2000, printed from the Internet on Mar. 2, 2012.*
Fujio et al., *Biosci. Biotech. Biochem.*, 61(6): 960-964 (1997).
European Patent Office, Extended European Search Report in European Patent Application No. 06782606.5 (Oct. 19, 2011).

* cited by examiner

*Primary Examiner* — Rosanne Kosson
(74) *Attorney, Agent, or Firm* — Leydig, Voit & Mayer, Ltd.

(57) ABSTRACT

A method of purifying cytidine diphosphate choline, which comprises contacting a cytidine diphosphate choline solution containing a nucleic acid analogue and having a pH of not less than 0.5 and not more than 5.0 with an H-type strongly acidic cation exchange resin, and eluting cytidine diphosphate choline adsorbed onto the resin with water or an aqueous solution having an ion concentration of not more than 0.1 mol/L to separate and purify the cytidine diphosphate choline.

6 Claims, No Drawings

METHOD OF PURIFYING CYTIDINE DIPHOSPHATE CHOLINE

TECHNICAL FIELD

The present invention relates to a method of purifying cytidine diphosphate choline. useful as a starting material of pharmaceutical products and a starting material of nutritious foods.

BACKGROUND Of THE INVENTION

As the method of purifying cytidine diphosphate choline (hereinafter to be abbreviated as CDP-choline), chemical synthetic methods (patent reference 1, patent reference 2) and methods using a culture of a microorganism or an enzyme (patent reference 3, patent reference 4) are known. As the method of purifying CDP-choline produced by a chemical synthetic method, a method using an anion exchange resin (patent reference 1) and a method using both of a strongly acidic ion exchange resin and a weakly basic ion exchange resin (patent reference 2) are known. In the latter method, two kinds of ion exchange resins are used. Moreover, while phosphorylcholine and cytidine-5'-monophosphate (hereinafter to be abbreviated as CMP) contained in a CDP-choline solution can be separated, uracil or uridine-5'-triphosphate (hereinafter to be abbreviated as UTP) cannot be separated efficiently by this method.

[patent reference 1] Japanese Published Examined Patent Application No. 6558/1988
[patent reference 2] Japanese Published Examined Patent Application No.31306/1994
[patent reference 3] Japanese Patent No. 3369236
[patent reference 4] WO99/49073

BRIEF SUMMWRY OF THE INVENTION

Problems to be Solved by the Invention

An object of the present invention is to provide a method of purifying CDP-choline, in which method CDP-choline can be separated from a nucleic acid analogue conveniently.

Means of Solving the Problems

The present invention relates to the following (1)-(6).
(1) A method of purifying CDP-choline, which comprises contacting a CDP-choline solution containing a nucleic acid analogue and having a pH of not less than 0.5 and not more than 5.0 with an H-type strongly acidic cation exchange resin, and eluting CDP-choline adsorbed onto the resin with water or an aqueous solution having an ion concentration of not more than 0.1 mol/L to separate and purify CDP-choline.
(2) The method of the above-mentioned (1), wherein the CDP-choline solution is prepared from a resulting medium containing CDP-choline, which has been produced and accumulated therein by placing a biocatalyst having an activity to produce CDP-choline from a precursor of UTP and choline or phosphorylcholine in an aqueous medium together with the precursor of UTP and choline or phosphorylcholine or a salt thereof.
(3) The method of the above-mentioned (2), wherein the biocatalyst comprises a culture or a treated culture of a microorganism capable of producing UTP from a precursor of UTP, and a culture or a treated culture of a microorganism capable of producing CDP-choline from UTP and choline or phosphorylcholine.
(4) The method of the above-mentioned (2), wherein the biocatalyst comprises an enzyme that catalyzes a reaction to produce CDP-choline from a precursor of UTP and choline or phosphorylcholine.
(5) The method of the above-mentioned (4), wherein the enzyme that catalyzes a reaction to produce CDP-choline is an enzyme selected from the group consisting of orotate phosphoribosyl transferase, orotidine-5'-monophosphate decarboxylase, uridine phosphorylase, uracil phosphoribosyltransferase, uridine kinase, uridylate and cytidylate kinases, nucleoside diphosphate kinase, cytidine-5'-triphosphate synthase, choline phosphate cytidyltransferase and choline kinase.
(6) The method of any of the above-mentioned (1) to (5), wherein the nucleic acid analogue is selected from uracil and UTP.

Effect of the Invention

The present invention provides CDP-choline and a salt thereof at a low cost.

DETAILED DESCRIPTION OF THE INVENTION

The CDP-choline solution to be used in the present invention may be prepared by any method as long as it contains a nucleic acid analogue and has a pH of not less than 0.5 and not more than 5.0. When the prepared CDP-choline solution has a pH of 0.5-5.0, it is directly used. When the pH is higher than 5.0, an acid such as hydrochloric acid, sulfuric acid, nitric acid, phosphoric acid and the like, is added, and when the pH is lower than 0.5, an alkali such as sodium hydroxide, potassium hydroxide and the like is added to adjust to pH 0.5-5.0, preferably 1.0-3.5, before use.

The H-type strongly acidic cation exchange resin may be of a gel type or a porous type, as long as it is an H-type strongly acidic cation exchange resin. Specific examples thereof include the Dowex series (e.g., HCR-S, HCR-W2, Marathon C, Monosphere 650C, MSC-1, Monosphere 88, 50W×2, 50W×4, 50W×8 etc.) manufactured by Dow Chemical Company, Diaion SK series (e.g., SK1B, SK104, SK110, SK112 etc.) manufactured by Mitsubishi chemical, Diaion PK series (e.g., PK208, PK212, PK220, PK228 etc.) manufactured by Mitsubishi Chemical, Amberlite series (e.g., IR120B, IR124 etc.) manufactured by Rohm and Haas and the like.

Degree of crosslinking of the H-type strongly acidic cation exchange resin is not particularly limited as long as CDP-choline and nucleic acid analogue can be separated at the degree of crosslinking. It is preferably 2-10%, more preferably 4-6%.

In the present invention, the H-type strongly acidic cation exchange resin is preferably used in the form of a packed column, and as the column to be used in the present invention, any column may be used.

The CDP-choline solution containing a nucleic acid analogue and having a pH of not less than 0.5 and not more than 5.0 is contacted with the H-type strongly acidic cation exchange resin by applying the solution to a column packed with the resin and the like to allow adsorption of CDP-choline onto the resin. For example, when the solution is applied to a column packed with an H-type strongly acidic cation exchange resin having a degree of crosslinking of 2-10%, the flow rate (SV) is 0.1-5.0, preferably 0.2-3.0.

By the above-mentioned adsorption treatment, a nucleic acid analogue contained in the solution, particularly a pyrimidine type nucleic acid substance such as orotic acid, orotidine-5'-monophosphate (hereinafter to be abbreviated as OMP), uridine-5'-monophosphate (hereinafter to be abbreviated as UMP), uridine-5'-diphosphate (hereinafter to be abbreviated as UDP), UTP, CMP, cytidine-5'-diphosphate (hereinafter to be abbreviated as CDP), cytidine-5'-triphosphate (hereinafter to be abbreviated as CTP) and the like can be efficiently separated or removed from CDP-choline. Out of the nucleic acid analogues, uracil and UTP are particularly preferably separated and removed, since they hardly adsorb to or do not at all adsorb to the resin, when a CDP-choline solution containing uracil and UTP is brought into contact with the resin at a pH of not less than 0.5 and not more than 5.0.

CDP-choline adsorbed on the H-type strongly acidic cation exchange resin is eluted by applying an aqueous solution having an ion concentration of not more than 0.1 mol/L, preferably not more than 0.03 mol/L, more preferably water, and the like, whereby CDP-choline is eluted from the resin, for the separation and purification.

Where necessary, the CDP-choline-containing solution collected by the above-mentioned elution step may be subjected to an activated carbon treatment or decolorization treatment using a nonpolar porous synthetic adsorbent, for example, Diaion HP series (e.g., HP20, HP21 etc.) manufactured by Mitsubishi Chemical, Diaion SP800 series (e.g., SP825, SP850 etc.) manufactured by Mitsubishi Chemical, Diaion SP200 series (e.g., SP207 etc.) manufactured by Mitsubishi Chemical, Amberlite XAD series (e.g., XAD4, XAD7HP, XAD16HP, XAD1180, XAD2000 etc.) manufactured by Rohm and Haas and the like.

The above-mentioned CDP-choline-containing solution or decolorized solution is adjusted to pH 2.0-4.0 with acid or alkali. After concentration is carried out as necessary, the concentration of CDP-choline is adjusted to 50-800 g/L, preferably 100-700 g/L, and crystals of CDP-choline can be obtained using an organic solvent, preferably a hydrophilic organic solvent such as acetone, ethanol, methanol, propanol and the like.

In addition, the above-mentioned CDP-choline-containing solution or decolorized solution is adjusted to pH 5.0-9.5 with sodium hydroxide. After concentration is carried out as necessary, the concentration of CDP-choline is adjusted to 50-800 g/L, preferably 100-700 g/L, and crystals of CDP-choline sodium salt can be obtained using an organic solvent, preferably a hydrophilic organic solvent such as acetone, ethanol, methanol, propanol and the like.

Examples of the method of obtaining CDP-choline crystals using an organic solvent include a method comprising adding an organic solvent to a CDP-choline solution to allow precipitation of crystals, and a method comprising adding dropwise a CDP-choline solution to a large amount of an organic solvent to allow precipitation of crystals.

In the present invention, the CDP-choline solution containing a nucleic acid analogue may be any as long as it is a solution containing CDP-choline and a nucleic acid analogue. Examples thereof include a solution produced by a chemical synthetic method, a method using a biocatalyst having an activity to produce CDP-choline from a precursor of UTP and choline or phosphorylcholine (hereinafter to be abbreviated as CDP-choline-producing activity).

Examples of the biocatalyst include a culture of a microorganism having a CDP-choline-producing activity, a treated culture thereof, an enzyme that catalyzes a reaction to produce CDP-choline and the like.

As the microorganism, any microorganism can be used as long as it has a CDP-choline-producing activity. A microorganism inherently having a CDP-choline-producing activity can be used as it is for the production of CDP-choline, and a microorganism naturally having no CDP-choline-producing activity can be used for the production of CDP-choline by introducing a DNA encoding an enzyme that catalyzes a reaction to produce CDP-choline from a precursor of UTP and choline or phosphocholine. Preferable examples of the microorganism include microorganisms belonging to the genera *Escherichia, Serratia, Bacillus, Brevibacterium, Corynebacterium, Microbacterium, Pseudomonas, Streptococcus, Sinorhizobium, Haemophilus, Arthrobacter, Aureobacterium, Cellulomonas, Clavibacter, Curtobacterium, Pimerobacter, Saccharomyces, Schizosaccharomyces, Kluyveromyces, Trichosporon, Schwanniomyces, Pichia, Candida* and the like.

Examples of the microorganism belonging to the genus *Escherichia* include microorganisms belonging to *Escherichia coli* such as *Escherichia coli* MM294, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* GI698, *Escherichia coli* TB1 and the like. Examples of the microorganism belonging to the genus *Serratia* include *Serratia ficaria, Serratia fonticola, Serratia liquefaciens, Serratia marcescens* and the like. Examples of the microorganism belonging to the genus *Bacillus* include *Bacillus subtilis, Bacillus megaterium, Bacillus amyloliquefaciens* and the like. Examples of the microorganism belonging to the genus *Brevibacterium* include *Brevibacterium immariophilum, Brevibacterium saccharolyticum, Brevibacterium flavum, Brevibacterium lactofermentum* and the like. Examples of the microorganism belonging to the genus *Corynebacterium* include microorganisms belonging to *Corynebacterium glutamicum* such as *Corynebacterium glutamicum* ATCC13032, *Corynebacterium glutamicum* ATCC13869 and the like, microorganisms belonging to *Corynebacterium ammoniagenes* such as *Corynebacterium ammoniagenes* ATCC6872, *Corynebacterium ammoniagenes* ATCC21170 and the like, microorganisms belonging to *Corynebacterium acetoacidophilum* such as *Corynebacterium acetoacidophilum* ATCC13870, etc. and the like. Examples of the microorganism belonging to the genus *Microbacterium* include microorganisms belonging to *Microbacterium ammoniaphilum* such as *Microbacterium ammoniaphilum* ATCC15354 and the like, *Microbacterium lactium, Microbacterium imperiale* and the like. Examples of the microorganism belonging to the genus *Pseudomonas* include *Pseudomonas putida* and the like. Examples of the microorganism belonging to the genus *Streptococcus* include *Streptococcus pneumoniae* and the like. Examples of the microorganism belonging to the genus *Sinorhizobium* include *Sinorhizobium meliloti* and the like. Examples of the microorganism belonging to the genus *Haemophilus* include *Haemophilus influenzae* and the like. Examples of the microorganism belonging to the genus *Arthrobacter* include *Arthrobacter citreus, Arthrobacter globiformis* and the like. Examples of the microorganism belonging to the genus *Aureobacterium* include *Aureobacterium flavescens, Aureobacterium saperdae, Aureobacterium testaceum* and the like. Examples of the microorganism belonging to the genus *Cellulomonas* include *Cellulomonas flavigena, Cellulomonas carta* and the like. Examples of the microorganism belonging to the genus *Clavibacter* include *Clavibacter michiganensis, Clavibacter rathayi* and the like. Examples of the microorganism belonging to the genus *Curtobacterium* include *Curtobacterium albidum, Curtobacte-*

*rium citreum, Curtobacterium luteum* and the like. Examples of the microorganism belonging to the genus *Pimerobacter* include *Pimerobacter simplex* and the like.

Examples of the microorganism belonging to the genus *Saccharomyces* include *Saccharomyces cerevisiae* and the like. Examples of the microorganism belonging to the genus *Schizosaccharomyces* include *Schizosaccharomyces pombe* and the like. Examples of the microorganism belonging to the genus *Kluyveromyces* include *Kluyveromyces lactis* and the like. Examples of the microorganism belonging to the genus *Trichosporon* include *Trichosporon pullulans* and the like. Examples of the microorganism belonging to the genus *Schwanniomyces* include *Schwanniomyces alluvius* and the like. Examples of the microorganism belonging to the genus *Pichia* include *Pichia pastoris* and the like. Examples of the microorganism belonging to the genus *Candida* include *Candida utilis* and the like.

In addition, more preferable examples of the microorganism include microorganisms belonging to the genera *Escherichia, Bacillus, Brevibacterium, Corynebacterium* and *Saccharomyces*, further preferably, microorganisms belonging to the genera *Escherichia, Brevibacterium, Corynebacterium* .

Of the above-mentioned microorganisms, when a microorganism naturally having a CDP-choline-producing activity has only an insufficient CDP-choline-producing activity, a recombinant DNA having a DNA encoding an enzyme that catalyzes a reaction to produce CDP-choline from a precursor of UTP and choline or phosphorylcholine may be introduced into the microorganism according to a conventional method, or a cell of different microorganism having the activity may be fused therewith to prepare a microorganism having an enhanced activity.

As the microorganism having an enhanced activity or a microorganism imparted with the activity, a transformant obtained by introducing a DNA encoding an enzyme that catalyzes the reaction into a microorganism according to the following method can be preferably used.

Examples of the DNA encoding an enzyme that catalyzes a reaction to produce CDP-choline from a precursor of UTP and choline or phosphorylcholine (hereinafter to be abbreviated as a CDP-choline-producing enzyme) include DNAs encoding orotate phosphoribosyl transferase [EC 2.4.2.10] having an activity to produce OMP from orotic acid, orotidine-5'-monophosphate decarboxylase [EC 4.1.1.23] having an activity to produce UMP from OMP, uridine phosphorylase [EC 2.4.2.3] having an activity to produce uridine from uracil, uracil phosphoribosyltransferase [EC 2.4.2.9] having an activity to produce UMP from uracil, uridine kinase [EC 2.7.1.48] having an activity to produce UMP from uridine, uridylate and cytidylate kinases [EC 2.7.1.48] having an activity to produce UDP from UMP, nucleoside diphosphate kinase [EC 2.7.4.6] having an activity to produce UTP from UDP, cytidine-5'-triphosphate synthetase [EC 6.3.4.2] (hereinafter to be abbreviated as PyrG) having an activity to produce CTP from UTP, choline kinase [EC 2.7.1.32] (hereinafter to be abbreviated as CKI) having an activity to produce phosphorylcholine from choline and choline phosphate cytidyltransferase [EC 2.7.7.15] (hereinafter to be abbreviated as CCT) having an activity to produce CDP-choline from CTP and phosphorylcholine and the like.

Preferable examples of the DNA encoding a CDP-choline-producing enzyme include DNAs encoding PyrG, CKI and CCT.

A DNA encoding PyrG has been cloned from the chromosome of *Escherichia coli*, and its entire nucleotide sequence has been determined [J. Biol. Chem., 261, 5568 (1986)]. Examples of a recombinant having a DNA encoding PyrG include pMW6 [Biosci. Biotechnol. Biochem., 61, 956 (1997)], which is a plasmid having a 2426 bp NruI-PstI fragment containing a DNA encoding PyrG derived from *Escherichia coli* inserted into an SmaI-PstI site of a multicloning site of vector pUC8 of *Escherichia coli* [Gene, 19, 259 (1982)] and the like.

The entire nucleotide sequence of the DNA encoding CCT has been determined [Eur. J. Biochem., 169, 477 (1987)]. Examples of a recombinant DNA having a DNA encoding CCT include plasmid pCC41 [Biochemical, 60, 701 (1988)] having a 1296 bp DraI fragment containing a DNA encoding CCT derived from yeast inserted into a SmaI site of a multicloning site of vector pUC18 of *Escherichia coli* [Gene, 33, 103 (1985)] and the like.

A DNA encoding CKI has also been cloned from a chromosome of yeast in the same manner, and the entire nucleotide sequence thereof has been determined [J. Biol. Chem., 264, 2053 (1989)]. Examples of a recombinant DNA having a DNA encoding CKI include plasmid pCK1D [J. Biol. Chem., 264, 2053 (1989)] having a 2692 bp PstI-HindIII fragment containing a DNA encoding CKI derived from yeast inserted into a shuttle vector YEpM4 of yeast and *Escherichia coli*, [Mol. Cell. Biol., 7, 29 (1987)] and the like.

The above-mentioned plasmids can be isolated and purified from *Escherichia coli* having these plasmids, according to a known method [Nuc. Acids Res., 7, 1513 (1979)].

A biocatalyst having a CDP-choline-producing activity can be obtained by obtaining a DNA encoding a CDP-choline-producing enzyme from the plasmid obtained as mentioned above according to, for example, Molecular Cloning, A Laboratory Manual, Third Edition, Sambrook et al. edit, Cold Spring Harbor Laboratory (2001), incorporating the DNA into an expression vector to prepare a recombinant DNA, and transforming the above-mentioned microorganism as a host cell.

First, a DNA encoding PyrG, CCT or CKI is obtained from the above-mentioned plasmid pMW6, plasmid pCC41 or plasmid pCK1D and, based on the obtained DNA, a DNA fragment having a suitable length and containing a part encoding the polypeptide is prepared as necessary.

Where necessary, moreover, a DNA wherein nucleotide of the nucleotide sequence of a partial DNA fragment corresponding to a CDP-choline-producing enzyme are substituted so as to provide a codon optimal for the expression of a host cell is prepared. The DNA is useful for an efficient production of a CDP-choline-producing enzyme.

A recombinant vector is produced by inserting the DNA fragment or full-length DNA into the downstream of a promoter of a suitable expression vector. In this case, DNA encoding a CDP-choline-producing enzyme may be independently inserted into an expression vector, or plural DNAs may be inserted into the same expression vector.

The recombinant vector is introduced into a host cell suitable for the expression vector.

As the host cell, the above-mentioned microorganisms can be mentioned.

As the expression vector, one capable of autonomous replication or one capable of being incorporated into a chromosome in the host cell, and having a promoter at a site permitting transcription of a DNA encoding a CDP-choline-producing enzyme can be used.

When prokaryote such as bacterium and the like is used as a host cell, a recombinant vector having a DNA encoding a CDP-choline-producing enzyme is preferably autonomously replicatable in a prokaryote, as well as constituted with a promoter, a ribosome binding sequence, the DNA and a transcription termination sequence. A gene regulating the promoter may also be contained.

Examples of the expression vector include pBTrp2, pBTac1, pBTac2 (all commercially available from Boehringer Mannheim), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/58), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/60], pGKA2 [prepared from *Escherichia coli* IGKA2 (FERM BP-6798), Japanese Published Unexamined Patent Application No. 221091/60], pTerm2 (U.S. Pat. No. 4,686,191, U.S. Pat. No. 4,939,094, U.S. Pat. No. 5,160,735), pSupex, pUB110, pTP5, pC194, pEG400 [J. Bacteriol., 172, 2392 (1990)], pGEX (manufactured by Pharmacia), pET system (manufactured by Novagen) and the like.

As the promoter, any promoter can be used as long as it is functionable in the host cell. Examples of the promoter include those derived from *Escherichia coli*, phage and the like, such as trp promoter ($P_{trp}$), lac promoter, $P_L$ promoter, $P_R$ promoter, T7 promoter and the like. In addition, a promoter having an artificially altered design such as a promoter ($P_{trp} \times 2$) in which two $P_{trp}$ are sequently connected in tandem, tac promoter, lac T7 promoter and let I promoter, and the like can also be used.

It is preferable to use a plasmid in which the distance between a Shine-Dalgarno sequence (ribosome binding sequence) and an initiation codon is adjusted to a suitable distance (e.g., 6 to 18 bases).

In the recombinant vector of the present invention, a transcription termination sequence is not always necessarily for the expression of a DNA encoding a CDP-choline-producing enzyme. However, it is preferable to place a transcription termination sequence directly downstream the structure gene.

As a method of introducing the recombinant vector, any method can be used as long as a DNA can be introduced into the above-mentioned host cell. For example, a method using a calcium ion [Proc. Natl. Acad. Sci. USA, 69, 2110 (1972)], a protoplast method (Japanese Published Unexamined Patent Application No. 248394/1988), the method described in Gene, 17, 107 (1982) or Molecular & General Genetics, 168, 111 (1979) and the like can be used.

When a yeast is used as the host cell, for example, YEp13 (ATCC37115), YEp24 (ATCC37051), YCp50 (ATCC37419), pHS19, pHS15 and the like can be used as the expression vector.

As the promoter, any promoter can be used as long as it permits expression in a yeast strain. Examples of the promoter include promoters of genes of the glycolytic system such as hexose kinase and the like, PHO5 promoter, PGK promoter, GAP promoter, ADH promoter, gal 1 promoter, gal 10 promoter, heat shock polypeptide promoter, MFα1 promoter, CUP 1 promoter and the like.

As the method of introducing the recombinant vector, any method can be used as long as it introduces the DNA into a yeast. Examples thereof include an electroporation method [Methods Enzymol., 194, 182 (1990)], a spheroplast method [Proc. Natl. Acad. Sci. USA, 75, 1929 (1978)], a lithium acetate method [J. Bacteriology, 153, 163 (1983)], the method described in Proc. Natl. Acad. Sci. USA, 75, 1929 (1978) and the like.

When the microorganism has only a part of the CDP-choline-producing activity, two or more kinds of microorganisms may be combined as appropriate to afford a CDP-choline-producing activity, and used as the biocatalyst having a CDP-choline-producing activity. Even when the microorganism has a CDP-choline-producing activity, two or more kinds of microorganisms can be combined.

Two or more kinds of microorganisms to be combined may be selected from any of the above-mentioned microorganisms. Examples of the combination include a combination of microorganisms belonging to the same genus or different genera selected from the microorganisms belonging to the genera *Escherichia, Serratia, Bacillus, Brevibacterium, Corynebacterium, Microbacterium, Pseudomonas, Streptococcus, Sinorhizobium, Haemophilus, Arthrobacter, Aureobacterium, Cellulomonas, Clavibacter, Curtobacterium, Pimerobacter, Saccharomyces, Schizosaccharomyces, Kluyveromyces, Trichosporon, Schwanniomyces, Pichia* and *Candida*, and the like.

For example, a combination of the microorganism belonging to the genus *Corynebacterium* and a microorganism belonging to the genus *Escherichia* and the like can be mentioned. Specific example is a combination of *Corynebacterium ammoniagenes* ATCC21170 and *Escherichia coli* MM294/pCKG55 strain (FERM BP-3717) (Japanese Patent No. 3369236, U.S. Pat. No. 6,387,667) and the like.

The example of the culture of a microorganism having a CDP-choline-producing activity, which is one of the biocatalysts having a CDP-choline-producing activity, is a culture obtained by culturing, according to a conventional method, the microorganism obtained by the above-mentioned method.

When the microorganism is a prokaryote such as bacteria and the like or a eukaryote such as yeast and the like, any of a natural medium and a synthetic medium can be used as the medium used for culturing the microorganism as long as it contains a carbon source, a nitrogen source, inorganic salts and the like to be assimilated by the microorganism, and enables efficient culturing of the microorganism.

Any carbon source may be used as long as the microorganism can assimilate it, and glucose, fructose, sucrose, molasses containing them, carbohydrates such as starch and starch hydrolysate, organic acid such as acetic acid, propionic acid and the like, alcohols such as ethanol, propanol and the like, and the like can be used.

As the nitrogen source, ammonium salts of inorganic acid or organic acid such as ammonia, ammonium chloride, ammonium sulfate, ammonium acetate, ammonium phosphate and the like, other nitrogen-containing compounds, peptone, meat extract, yeast extract, corn steep liquor, casein hydrolysate, soybean cake and soybean cake hydrolysate, various bacterial cells obtained by fermentation and digests thereof, and the like can be used.

As the inorganic salt, monopotassium phosphate, dipotassium phosphate, magnesium phosphate, magnesium sulfate, sodium chloride, ferrous sulfate, manganese sulfate, copper sulfate, calcium carbonate and the like can be used.

Culturing is performed under aerobic conditions by, for example, shaking culturing, aerobic stirred culturing and the like. The culturing temperature is preferably 15° C.-40° C. and the culturing time is generally 16 hours-7 days. The pH is preferably maintained 3-9 during culturing. The pH is adjusted with inorganic or organic acid, alkali solution, urea, calcium carbonate, ammonia and the like.

When the microorganism is a transformant, and the recombinant DNA used for transforming the microorganism has an antibiotic-resistance gene, an antibiotic corresponding to the antibiotic-resistance gene possessed by the recombinant DNA may be added to the medium used for culturing the microorganism.

When a culture of two or more kinds of microorganisms or a treated culture is used as the biocatalyst, respective microorganisms are cultured separately or in the same medium according to the above-mentioned method and the resulting product can be used.

When two or more kinds of microorganisms are cultured in the same medium, these microorganisms may be cultured simultaneously, or one microorganism may be cultured and the rest of the microorganisms may be cultured in the same medium during the culture of the first microorganism or after completion of the culture thereof.

Examples of the treated culture of the microorganism include a surfactant-treated culture, organic solvent-treated culture or cytolytic enzyme-treated culture obtained by treating the culture of the microorganism obtained by the above-mentioned method with a surfactant, an organic solvent or a cytolytic enzyme such as lysozyme and the like. A surfactant, an organic solvent or a cytolytic enzyme may be used singly to treat the culture of the microorganism, or they may be combined to treat the culture of the microorganism. In addition, a concentrate or dried product of the culture of the microorganism, which is obtained by concentrating or drying, in a concentrating machine, a desiccator and the like, a culture of the microorganism obtained by the above-mentioned method, cells obtained by solid-liquid separation of the culture of the microorganism by filtration, centrifugation and the like, and the dried product of the cells obtained by drying the cells in a desiccator and the like can be mentioned. Furthermore, the surfactant-treated product, the organic solvent-treated product, the cytolytic enzyme-treated product and the like of the cells can be mentioned, which are obtained by treating the cells with a surfactant, an organic solvent or a cytolytic enzyme such as lysozyme and the like, or a combination of these treated products.

When two or more kinds of microorganisms are used, two or more kinds of treated cultures may be individually used as biocatalysts having the CDP-choline-producing activity, or a mixture obtained by mixing these treated products of the cultures may be used as the biocatalyst having a CDP-choline-producing activity.

CDP-choline can be produced by bringing the above-mentioned biocatalyst in contact with a precursor of UTP and choline or phosphorylcholine or a salt thereof in a medium to allow production and accumulation of CDP-choline in the medium and recovering CDP-choline from the medium.

Examples of the precursor of UTP include orotic acid, OMP, uracil, uridine, UMP, UDP and the like, with preference given to orotic acid and uracil.

A specific method of producing and accumulating CDP-choline comprises mixing the above-mentioned biocatalyst and the precursor of UTP and choline or phosphorylcholine or a salt thereof in a medium, adding other components as necessary to the obtained mixture and maintaining the mixture at 20-50° C. for 2-48 hours while keeping pH 5-11, more preferably 6-10.

The amount of the biocatalyst to be used varies depending on the specific activity and the like of the biocatalyst. For example, when the culture of the microorganism or the treated product of the culture is used as the biocatalyst, it is preferably used in an amount of 5-500 mg, preferably 10-300 mg, relative to 1 mg of choline chloride, as wet cells obtained by centrifuging the culture or the treated culture.

Examples of choline, phosphorylcholine and salts thereof include choline, choline halides such as choline chloride, choline bromide, choline iodide and the like, choline bicarbonate, choline methylsulfate, choline dihydrogen citrate, choline bitartrate, phosphorylcholine, phosphorylcholine halides such as phosphorylcholine chloride, etc. and the like, preferably choline or phosphorylcholine halide, more preferably choline chloride or phosphorylcholine chloride.

The precursor of UTP, choline, phosphorylcholine and salts thereof may be obtained by chemical synthesis, or obtained from an organism by a fermentation method and the like. In addition, it is not necessarily to purify them completely. Furthermore, all of these substrates are commercially available and can be obtained easily.

The concentration of the precursor of UTP, choline, phosphorylcholine and salts thereof is preferably 1 mmol/L-1 mol/L, more preferably 10-100 mmol/L.

Examples of other necessary components include energy donor necessary for producing CDP-choline, phosphate ion, magnesium ion, ammonium ion, surfactant, organic solvent and the like. Addition of these components is not necessary when they are provided in necessary quantities from a biocatalyst and the like.

As the energy donor, sugars such as glucose, fructose, sucrose and the like, molasses, starch hydrolysate and the like, and amino acids such as glycine, alanine and the like can be used. They are preferably used at the concentration of 0.02-2.0 mol/L.

As the phosphate ion, inorganic phosphate such as orthophosphoric acid, pyrophosphoric acid, polyphosphoric acid such as tripolyphosphoric acid, tetrapolyphosphoric acid and the like, polymetaphosphoric acid, monopotassium phosphate, dipotassium phosphate, monosodium phosphate, disodium phosphate, etc. and the like can be used. These phosphate ions are preferably used at a concentration of 10-500 mmol/L.

As the magnesium ion, inorganic magnesium salt such as magnesium sulfate, magnesium nitrate, magnesium chloride and the like, and organic magnesium salt such as magnesium citrate and the like can be used. Magnesium ion is preferably used at a concentration of 5-200 mmol/L.

As the ammonium ion, aqueous ammonia, ammonia gas, various inorganic or organic ammonia salts, yeast extract, corn steep liquor and the like can be used. In addition, an organic nutrient source such as glutamine, peptide containing glutamine, casamino acid and the like can also be used in place of ammonium ion. The concentration of these ammonium ions is preferably used at a concentration of 10 mmol/L-2 mol/L.

As the surfactant, an anionic surfactant such as sodium dioctylsulfosuccinate (e.g., Rapisol B-80, manufactured by NOF Corporation), lauroyl sarcosinate and the like, a nonionic surfactant such as polyoxyethylene cetyl ether (e.g., Nonion P-208, manufactured by NOF Corporation) and the like, tertiary amines such as alkyldimethylamine (e.g., tertiary amine FB, manufactured by NOF Corporation), etc. and the like can also be used as long as production of CDP-choline is promoted. These are used in the range of generally 0.1-100 g/L, preferably 1-50 g/L.

Examples of the organic solvent include xylene, toluene, aliphatic alcohol (methyl alcohol, ethyl alcohol, butyl alcohol, etc.), acetone, ethyl acetate, dimethyl sulfoxide and the like. These are used at a concentration of generally 0.1-100 mL/L, preferably 1-50 mL/L.

As the medium in which the biocatalyst is contacted with the precursor of UTP and choline or phosphorylcholine or a salt thereof, the medium for culturing the microorganism to be used as a biocatalyst, the culture of the microorganism, the supernatant of the culture and the like can be used, and an aqueous medium can also be used.

Examples of the aqueous medium include water and buffers such as phosphate buffer, HEPES (N-2-hydroxyethylpiperazine-N-ethanesulfonic acid) buffer, tris [tris(hydroxymethyl)aminomethane] hydrochloride buffer and the like.

Any organic solvent may be added to the medium as long as the reaction is not inhibited. Examples of the organic solvent include acetone, ethyl acetate, dimethyl sulfoxide, xylene, methyl alcohol, ethyl alcohol, butanol and the like.

Examples of the method of producing CDP-choline includes a method (Japanese Patent No. 3369236, U.S. Pat. No. 6,387,667) including producing CDP-choline using Corynebacterium ammoniagenes ATCC21170 and Escherichia coli MM294/pCKG55 strain (FERM BP-3717) as the biocatalyst.

Examples of the CDP-choline-producing enzyme include one or more enzymes selected from the group consisting of orotate phosphoribosyl transferase, orotidine-5'-monophosphate decarboxylase, uridine phosphorylase, uracil phosphoribosyltransferase, uridine kinase, uridylate and cytidylate kinases, nucleoside diphosphate kinase, PyrG, CCT and CKI.

A crude enzyme or a purified enzyme obtained by disrupting the microorganism having the above-mentioned enzyme activity with a homogenizer and the like, and further applying a general enzyme purification method such as salting out, isoelectric point precipitation, organic solvent precipitation, dialysis, various chromatography treatments and the like can be used as the CDP-choline-producing enzyme. In addition, the disrupted product of the microorganism may be used as it is as the above-mentioned enzyme.

In addition, the above-mentioned disrupted product of microorganism, crude enzyme or purified enzyme may be immobilized on a water-insoluble carrier, gel and the like, and used as the above-mentioned enzyme.

CDP-choline can be produced by bringing the above-mentioned enzyme in contact with the precursor of UTP and choline or phosphorylcholine or a salt thereof in the medium to produce and accumulate CDP-choline, and recovering CDP-choline from the medium.

A specific method of producing and accumulating CDP-choline comprises mixing the above-mentioned enzyme and the precursor of UTP and choline or phosphorylcholine or a salt thereof in a medium, adding other components as necessary to the obtained mixture and maintaining the mixture at 20-50° C. for 2-48 hours while keeping pH 5-11, more preferably 6-10.

The amount of the CDP-producing enzyme to be used varies depending on the specific activity and the like of the enzyme. For example, when the crude enzyme is used as the enzyme, it is preferably used in an amount of 1 μg-500 mg, preferably 10 μg-300 mg, relative to 1 mg of choline chloride.

The precursor of UTP, choline, phosphorylcholine, a salt thereof to be added and other components to be added as necessary when producing and accumulating CDP-choline using the CDP-choline-producing enzyme are similar to those used for producing and accumulating CDP-choline using the culture and the like of the microorganism as mentioned above. Furthermore, adenosine-5'-triphosphate and the like may be added as necessary as an energy donor, and 5-phosphoribosyl diphosphate may be further added.

As the medium in which the CDP-choline-producing enzyme is brought into contact with the precursor of UTP and choline or phosphorylcholine or a salt thereof, the medium used for culturing the microorganism to be used as the biocatalyst, the culture, the supernatant of the culture and the like of the microorganism may be used, or an aqueous medium may also be used.

Examples of the aqueous medium include water, buffers such as phosphate buffer, HEPES (N-2-hydroxyethylpiperazine-N-ethanesulfonic acid) buffer, tris [tris(hydroxymethyl)aminomethane] hydrochloride and the like.

For preparing the CDP-choline solution from the medium in which CDP-choline has been produced and accumulated as mentioned above, a solid may be separated and removed from the medium according to a method using membrane separation, filtration, centrifugation and the like.

Examples of the nucleic acid analogue contained in the CDP-choline solution prepared by the above-mentioned method include uracil, UTP and the like.

CDP-choline and nucleic acid analogs can be analyzed by a conventional method using high performance liquid chromatography (UV detection).

The present invention is explained in more detail in the following by referring to Examples, which are not to be construed as limitative.

EXAMPLE 1

Purification of CDP-Choline Using Strongly Acidic Cation Exchange Resin

CDP-choline (50 g; manufactured by Wako Pure Chemical Industries, Ltd.), uracil (2 g; manufactured by Nacalai Tesque) and UTP (1 g; manufactured by Nacalai Tesque) were dissolved in water to prepare 5 L of CDP-choline solution. The solution was adjusted to pH 3.0 with sulfuric acid and applied to a column packed with a strongly acidic cation exchange resin Diaion PK208 (H-type) (10 L) with a crosslinking degree of 4%. Subsequently, water was applied, and a fraction wherein each concentration of uracil and UTP was less than 0.1% (w/w) relative to CDP-choline was obtained as a result of analysis by high performance liquid chromatography. The CDP-choline fraction was concentrated to 100 mL, and ethanol (350 mL) was gradually added. The precipitated crystals were collected by filtration, washed with 100% ethanol solution, and dried under reduced pressure at 20° C. for 3 days. As the result, 40 g of CDP-choline crystals, wherein each concentration of uracil and UTP was less than 0.1% (w/w) relative to CDP-choline, were obtained.

EXAMPLE 2

Purification of CDP-Choline from Culture of Microorganism Having an Activity to Produce CDP-Choline Escherichia coli MM294/pCKG55 strain (FERM BP-3717) having enzyme activities of PyrG, CCT and CKI was inoculated to a test tube containing L medium (10 mL) [liquid medium containing bactotripton (10 g/L; manufactured by Difco), yeast extract (5 g/L; manufactured by Difco) and NaCl (5 g/L) and adjusted to pH 7.2] supplemented with ampicillin (50 μg/mL), and cultured with shaking at 25° C., 300 rpm for 24 hours. The culture thus obtained (20 mL) was inoculated to 2 L of conical flask with baffles containing L medium (400 mL) supplemented with ampicillin (50 μg/mL) and cultured with rotary shaking at 25° C., 190 rpm for 16 hours. The culture thus obtained (125 mL) was inoculated to a 5 L culture bath containing a liquid medium (2.5 L; nonadjusted pH) with a composition of glucose (5 g/L; separately sterilized), peptone (5 g/L; manufactured by Kyokuto Pharmaceutical Industrial), $Na_2HPO_4$ (6 g/L), $KH_2PO_4$ (3 g/L), NaCl (5 g/L), NH$_4$Cl (1 g/L), MgSO$_4$.7H$_2$O (250 mg/L; separately sterilized) and vitamin B1 (4 µg/L; separately sterilized), and cultured with shaking at 600 rpm under culture condition of airflow 2.5 L/minute, at 25° C. for 11 hours and then at 32° C. for 13 hours, while adjusting the mixture to pH 7.0 with 14% aqueous ammonia. During culturing, a feed solution having a composition of glucose (167 g/L), peptone (167 g/L) was fed with a peristaltic pump at a rate of 30 mL/hours during the period of from 11 hours to 24 hours from the start of the culturing.

On the other hand, *Corynebacterium•ammoniagenes* ATCC21170 strain having an activity to produce UTP from orotic acid was inoculated to a test tube containing a liquid medium (10 mL) having a composition of glucose (50 g/L), polypeptone (10 g/L; manufactured by Daigo Eiyo Chemicals), yeast extract (10 g/L; manufactured by Daigo Eiyo Chemicals), urea (5 g/L), (NH$_4$)$_2$SO$_4$ (5 g/L), KH$_2$PO$_4$ (1 g/L), K$_2$HPO$_4$ (3 g/L), MgSO$_4$.7H$_2$O (1 g/L), CaCl$_2$.2H$_2$O (0.1 g/L), FeSO$_4$.7H$_2$O (10 mg/L), ZnSO$_4$.7H$_2$O (10 mg/L), MnSO$_4$.4-6H$_2$O (20 mg/L), L-cysteine (20 mg/L), calcium D-pantothenate (10 mg/L), vitamin B1 (5 mg/L), nicotinic acid (5 mg/L) and biotin (30 µg/L; adjusted to pH 7.2 with sodium hydroxide), and cultured with reciprocal shaking at 300 rpm at 28° C. for 24 hours. The culture thus obtained (20 mL) was inoculated to a 2 L conical flask with baffle containing a liquid medium (230 mL) having the same composition as the above-mentioned, and cultured with rotary shaking at 190 rpm at 28° C. for 24 hours. The culture thus obtained (250 mL) was inoculated to a 5 L culture bath containing a liquid medium (2.5 L) having a composition of glucose (100 g/L), meat extract (10 g/L), polypeptone (10 g/L), KH$_2$PO$_4$ (1 g/L), K$_2$HPO$_4$ (1 g/L), MgSO$_4$.7H$_2$O (1 g/L), CaCl$_2$.2H$_2$O (0.1 g/L), FeSO$_4$.7H$_2$O (20 mg/L), ZnSO$_4$.7H$_2$O (10 mg/L), MnSO$_4$.4-6H$_2$O (20 mg/L), β-alanine (15 mg/L), L-cysteine (20 mg/L), biotin (100 µg/L), urea (2 g/L; separately sterilized) and vitamin B1 (5 mg/L; separately sterilized) (adjusted to pH 7.2 with sodium hydroxide) and seed-cultured with shaking at 600 rpm at 32° C. under culture condition of airflow 2.5 L/minute while adjusting the mixture to pH 6.8 with concentrated aqueous ammonia. At the time point when glucose in the supernatant of the above-mentioned seed-culture medium was consumed, the culture (350 mL) was aseptically collected, inoculated to a 5 L culture bath containing a liquid medium (2.5 L) having a composition of glucose (180 g/L), KH$_2$PO$_4$ (10 g/L), K$_2$HPO$_4$ (10 g/L), MgSO$_4$.7H$_2$O (10 g/L), CaCl$_2$.2H$_2$O (0.1 g/L), FeSO$_4$.7H$_2$O (20 mg/L), ZnSO$_4$.7H$_2$O (10 mg/L), MnSO$_4$.4-6H$_2$O (20 mg/L; separately sterilized), β-alanine (15 mg/L), L-cysteine (20 mg/L), sodium glutamate (1 g/L), biotin (100 µg/L), urea (2 g/L; separately sterilized) and vitamin B1 (5 mg/L; separately sterilized) (adjusted to pH 7.2 with sodium hydroxide) and main-cultured with shaking at 600 rpm at 32° C. under culture condition of airflow 2.5 L/minute while adjusting the mixture to pH 6.8 with concentrated aqueous ammonia. The culturing was ceased at the time point when glucose in the culture supernatant was consumed.

The culture (360 mL) of *Escherichia coli* MM294/pCKG55 strain and the culture (360 mL) of *Corynebacterium•ammoniagenes* ATCC21170 strain thus obtained were placed in a 2 L culture bath, glucose (100 g/L), orotic acid (10 g/L), choline chloride (8.4 g/L), MgSO$_4$.7H$_2$O (5 g/L) and xylene (20 mL/L) were added thereto, and distilled water was added to allow the total amount to be 800 mL. The mixture was reacted with shaking at 800 rpm at 32° C. under the condition of airflow 0.8 L/minute while adjusting the mixture to pH 7.2 with 10N sodium hydroxide. During the reaction, KH$_2$PO$_4$ was added as appropriate to keep the concentration of phosphoric acid in the supernatant of the reaction mixture at 1-5 g/L as KH$_2$PO$_4$. The reaction was carried out for 23 hours to obtain 11.0 g/L of CDP-choline.

Four batches of the above-mentioned reaction mixture were adjusted to pH 1.0 with sulfuric acid, cells were separated by centrifugation (7000 rpm, 10 min), and water was added to the obtained supernatant to make the total amount 6 L (CDP-choline 6.0 g/L, uracil 0.5 g/L, UTP 1.0 g/L). This cytidinediphosphoric choline solution was applied to a column packed with a strongly acidic cation exchange resin Diaion SK104 (H-type, 10 L) having a crosslinking degree of 4%. Subsequently, water was applied, and a fraction, in which each concentration of uracil, UTP was less than 0.1% (w/w) relative to CDP-choline (analyzed by high performance liquid chromatography) was collected. The CDP-choline fraction was decolorized using activated carbon, and then concentrated to 100 mL. Ethanol (350 mL) was gradually added to the concentrated solution, and the precipitated crystals were collected by filtration. The obtained crystals were washed with 100% ethanol solution, and then dried under reduced pressure at 20° C. for 3 days. As a result, CDP-choline crystals (18 g), in which each concentration of uracil, UTP was less than 0.1% (w/w) relative to CDP-choline, were obtained.

EXAMPLE 3

Purification of CDP-Choline Sodium Salt from a Culture of Microorganism Having an Ability to Produce CDP-Choline Four batches of the reaction mixture obtained in the same manner as in Example 2 were adjusted to pH 1.0 with sulfuric acid, cells were separated by centrifugation (7000 rpm, 10 min), and water was added to the obtained supernatant to make the total amount 6 L (CDP-choline 6.0 g/L, uracil 0.5 g/L, UTP 1.0 g/L). This cytidine diphosphate choline solution was applied to a column packed with a strongly acidic cation exchange resin Diaion SK104 (H-type, 10 L) having a crosslinking degree of 4%. Subsequently, water was applied, and a fraction, in which each concentration of uracil, UTP was less than 0.1% (w/w) relative to CDP-choline (analyzed by high performance liquid chromatography) was collected. The CDP-choline fraction was adjusted to pH 7.5 with sodium hydroxide, decolorized with activated carbon, and then concentrated to 100 mL. Ethanol (400 mL) was gradually added to the concentrated solution, and the precipitated crystals were collected by filtration. The obtained crystals were washed with 100% ethanol solution, and then dried under reduced pressure at 20° C. for 3 days. As a result, CDP-choline sodium salt crystals (20 g), in which each concentration of uracil, UTP was less than 0.1% (w/w) relative to CDP-choline, were obtained.

From the foregoing results, it has been clarified that CDP-choline or a salt thereof free from impurity can be obtained conveniently by treating a CDP-choline solution containing a nucleic acid analogue only once with a strongly acidic cation exchange resin.

Industrial Applicability

According to the present invention, CDP-choline and a salt thereof are provided at a low cost.

The invention claimed is:
1. A method of purifying cytidine diphosphate choline (CDP-choline), which method comprises
   a) contacting a CDP-choline solution having a pH of 0.5 to 5.0 and containing an impurity comprising a nucleic acid analogue with an H-type strongly acidic cation exchange resin of a gel type or a porous type which has a degree of crosslinking of 2-10%, wherein the CDP-choline binds to the resin and the nucleic acid analogue does not bind to the resin, and b) eluting the CDP-choline adsorbed onto the resin with water or an aqueous solution having an ion concentration of not more than 0.1 mol/L, thereby purifying CDP-choline from the nucleic acid analogue.

2. The method of claim 1, wherein the CDP-choline solution is prepared from a resulting medium containing CDP-choline, which has been produced and accumulated therein by bringing a biocatalyst having an activity to produce CDP-choline from a precursor of uridine-5'-triphosphate (UTP) and choline or phosphorylcholine in an aqueous medium into contact with the precursor of UTP and choline or phosphorylcholine or a salt thereof.

3. The method of claim 2, wherein the biocatalyst comprises a culture or a treated culture of a microorganism capable of producing UTP from a precursor of UTP, and a culture or a treated culture of a microorganism capable of producing CDP-choline from UTP and choline or phosphorylcholine.

4. The method of claim 2, wherein the biocatalyst comprises an enzyme that catalyzes a reaction to produce CDP-choline from a precursor of UTP and choline or phosphorylcholine.

5. The method of claim 4, wherein the enzyme that catalyzes a reaction to produce CDP-choline is an enzyme selected from the group consisting of orotate phosphoribosyl transferase, orotidine-5'-monophosphate decarboxylase, uridine phosphorylase, uracil phosphoribosyltransferase, uridine kinase, uridylate and cytidylate kinases, nucleoside diphosphate kinase, cytidine-5'-triphosphate synthase, choline phosphate cytidyltransferase and choline kinase.

6. The method of claim 1, wherein the nucleic acid analogue is selected from uracil and UTP.

* * * * *